(12) United States Patent
Geistert

(10) Patent No.: US 7,507,237 B2
(45) Date of Patent: Mar. 24, 2009

(54) CATHETER

(75) Inventor: Wolfgang Geistert, Rheinfelden (DE)

(73) Assignee: Biotronik GmbH & Co. KG (DE)

( * ) Notice: Subject to any disclaimer, the term of this patent is extended or adjusted under 35 U.S.C. 154(b) by 463 days.

(21) Appl. No.: 10/939,089

(22) Filed: Sep. 10, 2004

(65) Prior Publication Data

US 2005/0065511 A1    Mar. 24, 2005

(30) Foreign Application Priority Data

Sep. 11, 2003   (DE) ............................... 103 42 709

(51) Int. Cl.
*A61B 18/14* (2006.01)
*A61B 5/04* (2006.01)

(52) U.S. Cl. ........................ 606/41; 600/374
(58) Field of Classification Search ................ 606/41; 600/374

See application file for complete search history.

(56) References Cited

U.S. PATENT DOCUMENTS

| 5,281,215 A | 1/1994 | Milder |
| 5,348,554 A | 9/1994 | Imran et al. |
| 5,520,684 A * | 5/1996 | Imran .......................... 606/41 |
| 5,540,681 A | 7/1996 | Strul et al. |
| 5,755,760 A | 5/1998 | Maguire et al. |
| 5,980,515 A | 11/1999 | Tu |
| 6,497,721 B2 * | 12/2002 | Ginsburg et al. ............ 607/106 |
| 2003/0004506 A1 | 1/2003 | Messing |

FOREIGN PATENT DOCUMENTS

| DE | 696 16 541 | 7/2002 |
| EP | 1 008 327 | 6/2000 |
| WO | WO 93/08755 | 5/1993 |
| WO | WO 93/20769 | 10/1993 |

\* cited by examiner

*Primary Examiner*—Lee S Cohen
(74) *Attorney, Agent, or Firm*—Hahn Loeser & Parks LLP

(57) ABSTRACT

The invention concerns a catheter for intravascular application, comprising a shaft extending along the catheter longitudinal axis from the proximal end to the distal end and having a fluid-tight shaft wall and at least one lumen which is adapted to guide a fluid and at least one electrically conductive wire which extends from the proximal end at least into the proximity of the distal end of the catheter along the catheter longitudinal axis. The catheter is characterized in that on at least one portion length of the catheter which is provided for introduction into a body, a lower level of heat-transmission resistance obtains between a fluid in the lumen and the electrically conductive wire than between the wire and the shaft wall so that heat produced in the wire can be effectively dissipated to a fluid flowing in the lumen, wherein the catheter includes at least one temperature sensor which is arranged to detect a temperature which in the case of heating of the wire depends at least predominantly on the heating of the wire.

18 Claims, 4 Drawing Sheets

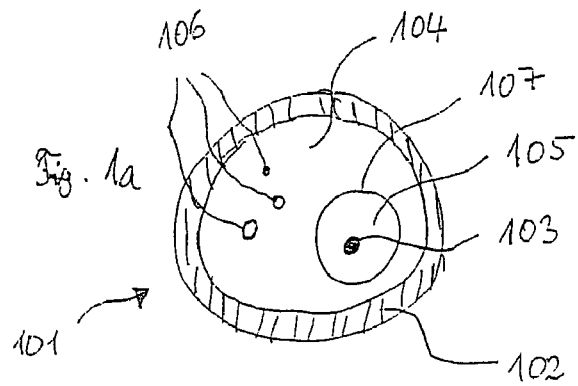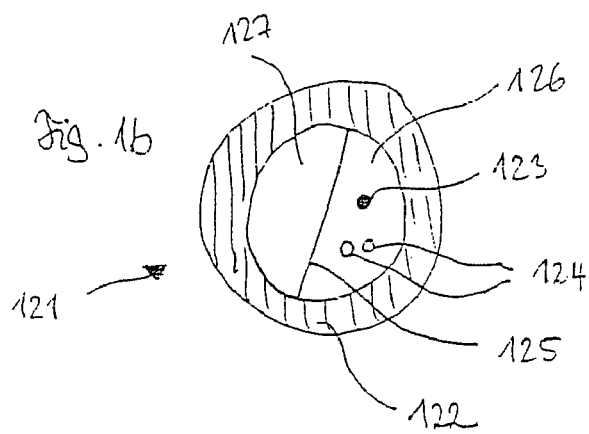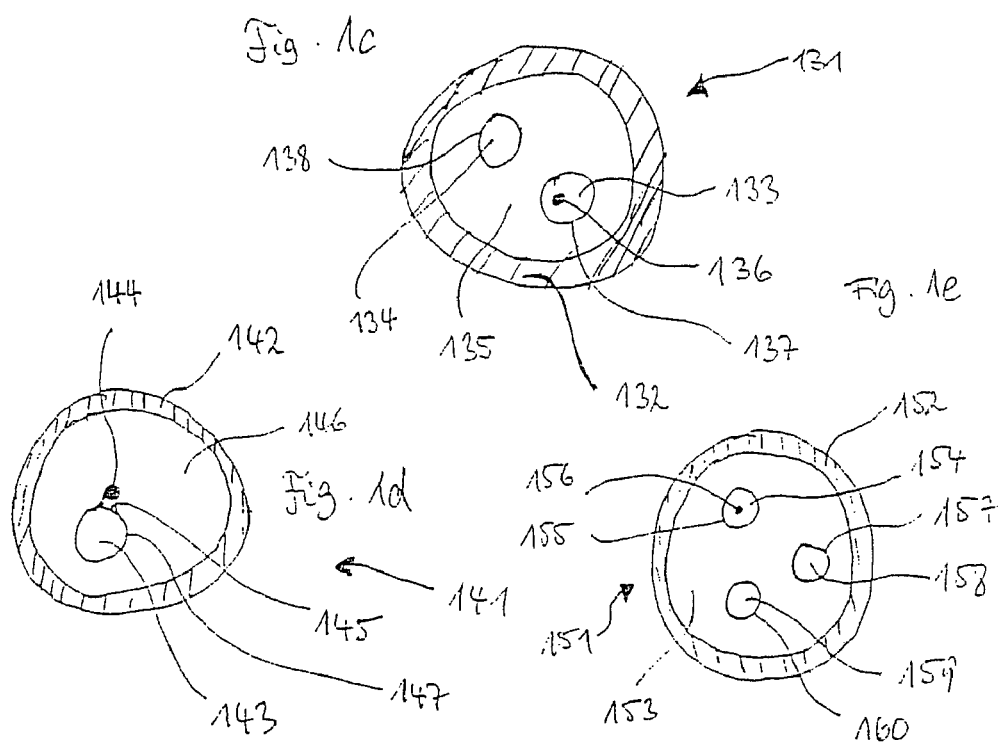

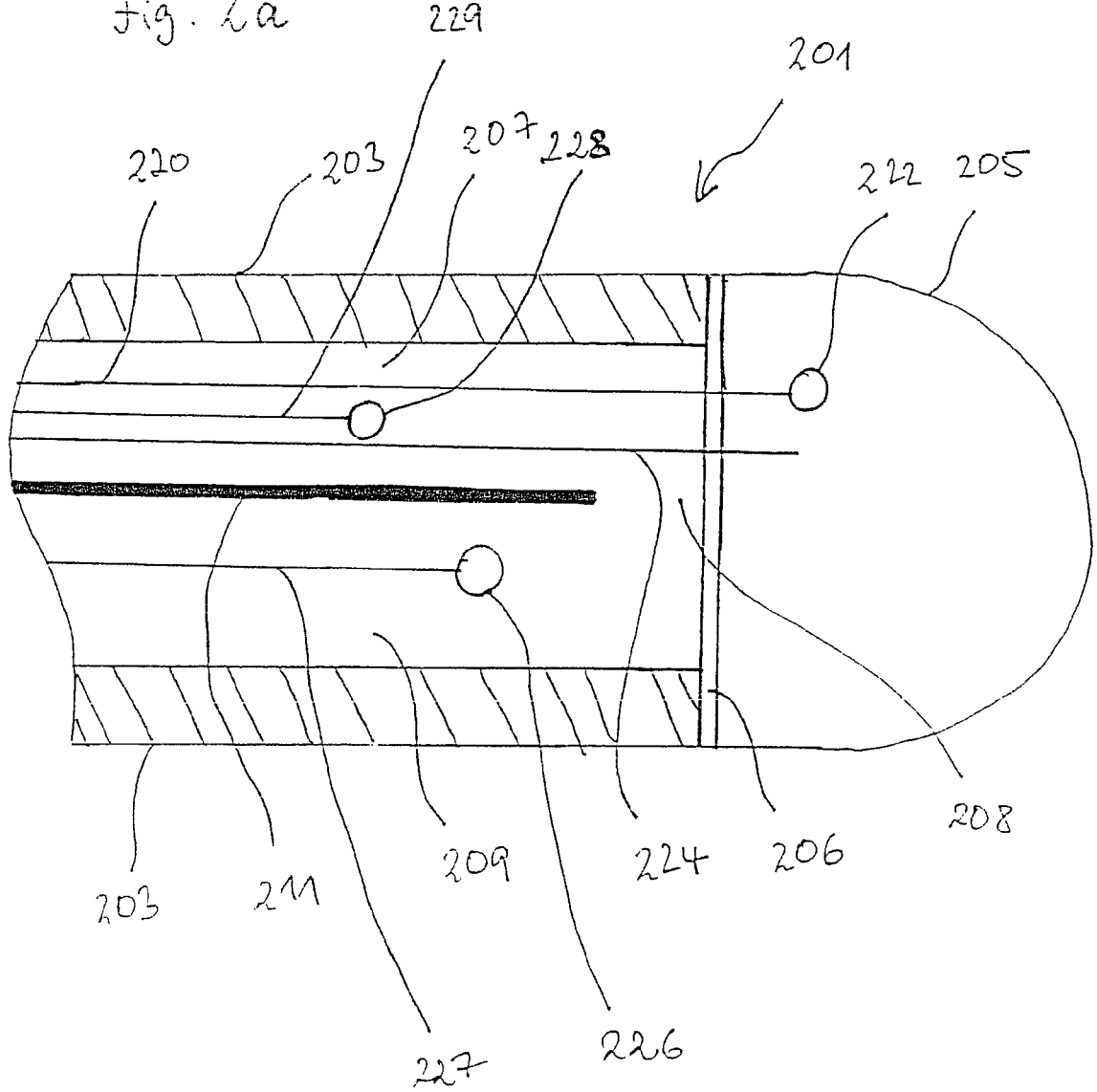

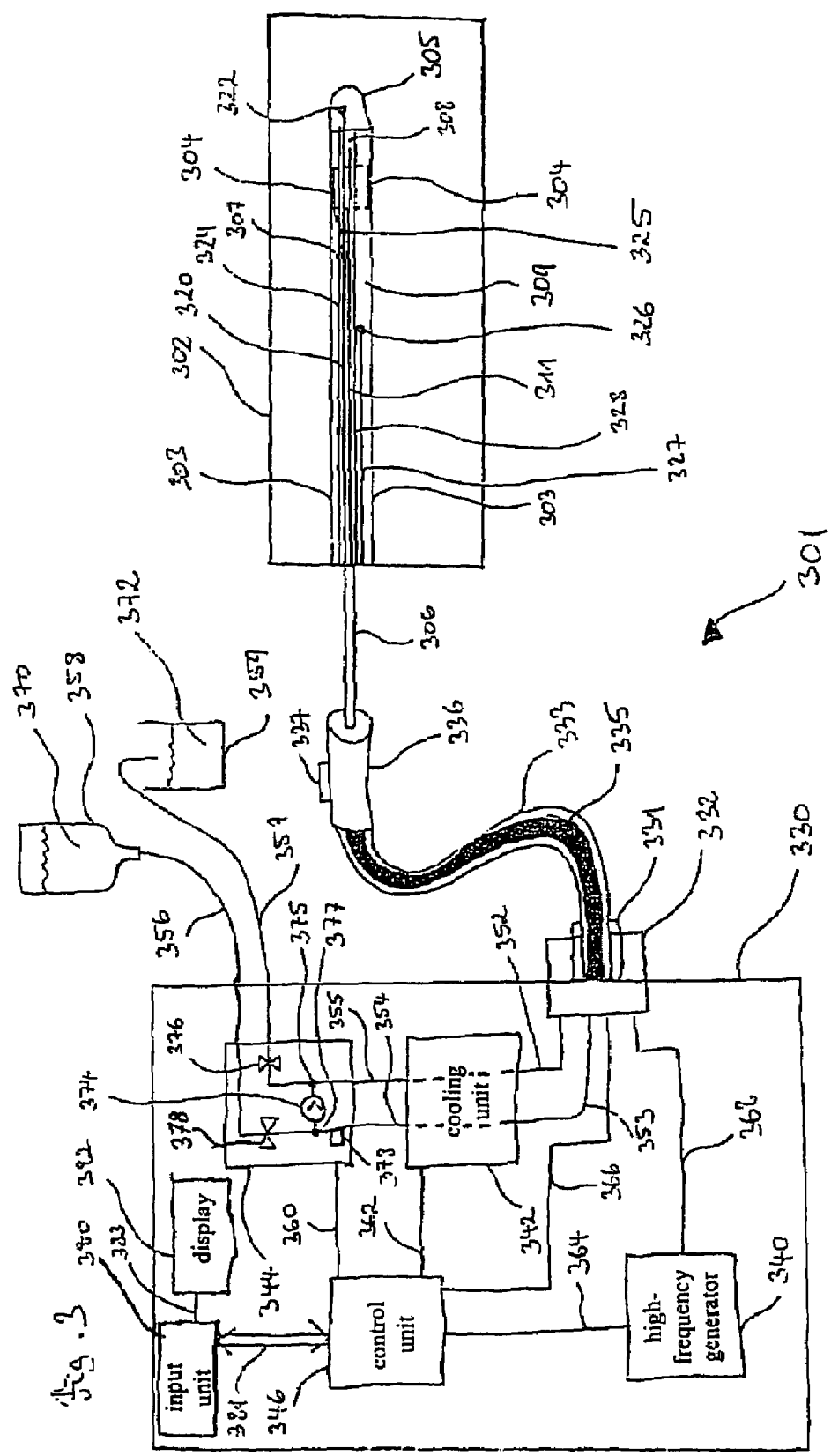

CATHETER

BACKGROUND OF THE INVENTION

The invention concerns a catheter for intravascular application, with a proximal and a distal end and a catheter longitudinal axis, comprising a shaft extending along the catheter longitudinal axis from the proximal end to the distal end and having a fluid-tight shaft wall and at least one lumen which is adapted to guide a fluid, which extends from the proximal end at least into the proximity of the distal end of the catheter, and which is enclosed by the shaft. The catheter also has at least one electrically conductive wire which extends from the proximal end at least into the proximity of the distal end of the catheter along the catheter longitudinal axis.

The state of the art discloses catheters which include wires in the form of control wires for deflecting the distal end of a catheter, or electrical feed lines for electrodes, for example high-frequency lines in the case of ablation catheters or also in the form of electrical feed lines for sensors. The wires, in the form of control wires or electrical feed lines, are usually guided in the interior of a catheter shaft.

Those catheters which are known from the state of the art involve the problem that the wires which extend in the catheter shaft, when using the catheter during a magnetic resonance tomography, are significantly heated by high, electromagnetically-induced currents, so that the conduction of heat results in a rise in the temperature of the catheter shaft, which entails the risk of coagulation along the catheter shaft.

In the case of ablation catheters, there is equally the risk of coagulation phenomena along the catheter shaft disposed in the body, due to high, high-frequency currents which are passed in the feed lines to the ablation electrode and which result in an increase in the temperature of the feed lines and, by way of heat conduction, an increase in the temperature of the catheter shaft.

DE 693 32 414 T2 discloses a cryogenic catheter which has lumens for guiding a coolant and temperature sensors at the distal end for monitoring the temperature of an ablation electrode and the coolant.

U.S. No 2003/0004506 and U.S. Pat. No. 5,348,554 disclose catheters having a fluid-cooled ablation electrode.

U.S. Pat. No. 5,980,515 discloses a catheter with a rotating saw tool and a flushing device, wherein the flushing device can also serve for cooling an ablation electrode.

The problem of catheter shaft heating due to electrically conductive wires extending in the shaft is not referred to in those patent specifications and is also not resolved.

SUMMARY OF THE INVENTION

The object of the present invention is that of providing a catheter in which the above-described problem of catheter shaft heating due to electrically conductive wires extending in the shaft does not occur, in particular when applying magnetic resonance tomography.

That object is attained by a catheter of the kind set forth in the opening part of this specification in which on at least one portion length of the catheter which is provided for introduction into a body, a lower level of heat-transmission resistance obtains between a fluid in the lumen and conductive wire than between the wire and the shaft wall so that heat produced in the wire can be effectively dissipated to the fluid flowing in the lumen. For that purpose the catheter includes a temperature sensor which is arranged to detect a temperature which in the case of heating of the wire depends at least predominantly on the heating of the wire.

The temperature sensor can be heat-conductingly connected to the wire. The term "heat-conductingly connected" is used here to denote both transmission of heat by way of atomic vibrations and also transmission of heat by way of mass transport. The heat-conducting connection can thus include both convective conduction and also phonon conduction.

The temperature sensor is arranged for example, at a location spaced from the distal end, for directly or indirectly detecting a temperature of the shaft wall, on the basis of heat produced in the wire, on the portion of the shaft which is provided for introduction into a body and at which the shaft wall temperature depends substantially on the wire temperature.

For direct detection of the shaft wall temperature, the temperature sensor is arranged on or in the shaft wall. With that arrangement, the risk of forming coagulation phenomena can be derived directly from a shaft wall temperature value.

For indirect detection of the shaft wall temperature, the temperature sensor can be arranged on the heat-transmission section from the wire to the shaft wall.

For example, the temperature sensor is arranged on the wire or in the wire or is formed by the wire itself. In that arrangement, the shaft wall temperature can be calculated or ascertained empirically. For indirect detection of the shaft wall temperature, the temperature sensor can be arranged in a wire-guiding lumen and can there detect the temperature of a fluid. In that case also, the shaft wall temperature can be calculated or ascertained empirically.

In the case of an ablation catheter, the temperature sensor is arranged at a sufficient spacing from an ablation electrode disposed at the distal end of the catheter, in such a way that the heat discharged by the ablation electrode does not influence temperature measurement of the shaft rise in temperature caused by the wires. Therefore, in accordance with the invention, "spaced from the ablation electrode" means arranged to be sufficiently heat-insulated from the ablation electrode.

Cooling of the wire by way of the fluid advantageously provides that the discharge of heat from the catheter shaft to the medium surrounding the catheter shaft is reduced. The temperature sensor advantageously makes it possible to monitor the catheter shaft temperature, preferably by an arrangement for detecting the fluid temperature.

In a preferred embodiment, the catheter has a first and a second lumen, which are adapted to carry a fluid and which extend from the proximal end of the catheter into the proximity of the distal end thereof and which are enclosed by the shaft. In the region of the distal end, the catheter has a fluid passage between the first lumen and the second lumen so that the fluid can flow in one lumen in the direction of the distal end and from there back to the proximal end in the fluid passage and the second lumen.

This embodiment can advantageously implement a closed cooling circuit.

In the proximity of the distal end, the catheter can have at least one opening which is in fluid communication with at least one of the lumens and which is so designed that fluid can flow outwardly from the catheter.

The embodiment of the catheter with two lumens can have at least one opening at the distal end by way of which the fluid can flow outwardly. In this embodiment, the catheter has a fluid flow guide means formed by the lumens with an outlet at the distal end for cooling of the ablation electrode and/or the tissue surrounding the tissue surrounding the electrode.

Alternatively, the catheter can also be embodied with a unidirectional fluid guide means. Such an opening is already known in relation to ablation catheters from the state of the art, the opening in the catheter being arranged in such a way that heat produced at the ablation electrode can be partially dissipated to the fluid.

In a further embodiment, the distal end is adapted to feed exclusively a fluid flowing in a second lumen to the ablation electrode. This embodiment advantageously makes it possible to provide for separate cooling effects with respectively different temperature regulation values for wires to be cooled and the ablation electrode. The catheter in this embodiment has three separate lumens. A first lumen is in the form of a wire-guiding lumen, in which wires to be cooled are arranged along the longitudinal axis of the catheter. The temperature sensor in this embodiment is preferably arranged in the wire-guiding lumen or in the proximity thereof, with good thermal contact. In this case, the distal end is adapted to return the fluid used for cooling the wires by way of a third lumen. As an alternative thereto, the distal end is adapted either to cause the fluid used for cooling the ablation electrode to issue from the catheter by way of an opening or also to return it by way of the third lumen. As in that case, both the heat of the ablation electrode and also the heat of the wire is dissipated by way of the fluid flowing in the third lumen, when the temperature sensor is arranged outside the wire-guiding lumen, the level of heat-transmission resistance is greater between the third lumen and the temperature sensor than between the temperature sensor and the wire-guiding lumen.

In a further preferred feature, the second lumen and/or further lumens is or are disposed within the first lumen. The lumens can be formed by individual tubes. As an alternative thereto, the lumens can be formed along the longitudinal axis of the catheter by at least one separating wall in a tube and the fluid passage can be formed by at least one aperture. It is also possible to envisage an embodiment which has a combination of lumens separated by separating walls and lumens formed by individual tubes. There are three alternative configurations in regard to embodying the lumens in the interior of the catheter: the lumens can be embodied in mutually juxtaposed relationship, separated from each other by separating walls, in a tube. Alternatively, a plurality of tubes can be arranged in a casing lumen. Those tubes can be arranged in mutually juxtaposed relationship or one within the other (coaxial).

In a preferred embodiment, the wire is an electrical feed line. The electrical feed line can be in the form of a single-conductor or multi-conductor feed line, for example, in the form of a feed line for an ablation electrode or a feed line for sensors.

The wire can also be a control wire which is arranged in the interior of the lumen in the direction of the catheter longitudinal axis. Such a control wire can be arranged, for example, in a guide wire. Preferably the control wire is adapted to deflect the distal end of a catheter with a directional component transversely with respect to the catheter longitudinal axis. The distal end of the catheter can thereby be curved by way of the control wire and the catheter can thus be guided in curves within a lumen in a body. For that purpose, the control wire is fixed to the distal end of the catheter and is preferably arranged displaceably in the interior of the lumen in the direction of the catheter longitudinal axis. In accordance with the invention, a guide wire can also be of such a configuration, by means of a lumen, that it is to be cooled by means of a fluid. The rise in temperature of such a guide wire can be effected, in the case of magnetic resonance tomography, in that currents are induced in a conventional wire coil or a metal shaft of such a guide wire. Due to a lumen, arranged in the interior of the wire coil, of a guide wire, the latter can be cooled and also represents a catheter in accordance with the invention.

The wire, heated by induction, of such a guide wire is thus, by way of example, a metal coil or a metal shaft of the guide wire.

In a preferred embodiment, the catheter has at least one temperature sensor for detecting the temperature of the fluid or the wire or the shaft wall.

The catheter can also have at least one temperature sensor for detecting the temperature of a fluid issuing at the proximal end of the catheter.

A temperature sensor can also be arranged along the catheter longitudinal axis in the region of the center of the catheter shaft portion which is provided for intracorporeal invasion. In the case, for example, of ablation catheters, that affords a sufficient spacing from an ablation electrode and the heat given off thereby.

A shaft of a catheter, in accordance with the invention, can have a plurality of temperature sensors arranged along the catheter longitudinal axis. The temperature sensors are arranged to detect the temperature of a wire and/or of the shaft wall and/or a lumen. By way of example, the temperature sensors are formed by a plurality of wires extending in a spiral configuration in the peripheral direction of the catheter shaft or by longitudinal wires extending along the longitudinal axis of the catheter, the wires extending in the spiral configuration and the longitudinal wires being adapted to not substantially heat up in a magnetic field of a magnetic resonance tomograph. For that purpose, the temperature sensors are preferably of a high-resistance nature.

In an alternative configuration, the catheter is an ablation catheter. For that purpose, at its distal end, the catheter includes an electrode which is electrically connected to the wire and by way of which a high-frequency electrical current can be delivered to tissue disposed in the area around the electrode. As a result, heat is produced in the tissue, by which the tissue is damaged or destroyed. Accordingly, in particular pathologically altered tissue can be specifically and targetedly destroyed with an ablation catheter in order thereby, for example, to locally block the conduction of cardiac action signals.

The catheter can also be a mapping catheter. For that purpose in the region of the distal end the catheter includes one or more sensing electrodes. The catheter can also be a pacemaker or defibrillation electrode.

In a preferred embodiment, the catheter is in the form of an ablation and mapping catheter, in which the features of an ablation catheter and those of a mapping catheter are embodied on just one catheter. For that purpose, besides at least one ablation electrode, the catheter includes at least one sensing electrode.

The invention also concerns an arrangement for intravascular invasion, including a catheter in accordance with one of the above-indicated embodiments and a fluid feed unit which is in fluid communication with at least one lumen of the catheter and adapted to produce a flow of fluid into the lumen.

Preferably, the arrangement also includes a temperature monitoring unit connected to at least one temperature sensor of the catheter.

The arrangement may also include a cooling unit which is in fluid communication with at least one lumen of the catheter and adapted to remove heat from a fluid. Preferably, the cooling unit is adapted to remove heat from the fluid in dependence on a cooling control signal. Further advantages are enjoyed if the cooling unit is adapted to alter the thermal power removed from the fluid in dependence on the control signal. For that purpose, the cooling unit may include at least one Peltier element. The arrangement can include a temperature regulating device for observing a predetermined fluid temperature, for example in a cooling circuit.

In an advantageous embodiment, the fluid feed unit includes a controllable pump unit which is in fluid communication at least with a lumen of the catheter and adapted to pump a fluid into the lumen in dependence on a fluid control signal. In a further advantageous feature, the pump unit can be adapted to pump a predetermined volume of fluid into the lumen per unit of time in dependence on the fluid control signal.

The fluid feed unit can also be formed by an arrangement with a fluid container and a feed conduit, wherein when the fluid container is arranged at a higher level in relation to the catheter, as in the case of an infusion drip, the fluid can flow downwardly into the catheter.

In an alternative embodiment, the arrangement has a cooling circuit in which the pump unit and the cooling unit are contained, and a temperature monitoring unit, wherein the temperature monitoring unit is operatively connected to at least one temperature sensor, the pump unit or the cooling unit or both. The temperature sensor is adapted to produce a temperature signal representative of a temperature and the temperature monitoring unit is adapted to evaluate a temperature signal produced by the temperature sensor and to control the pump unit or the cooling unit or both in accordance with a regulating algorithm predetermined in the temperature monitoring unit and to produce control signals corresponding thereto.

BRIEF DESCRIPTION OF THE DRAWINGS

FIG. 1 shows diagrammatically illustrated cross-sections through possible embodiments of a catheter, FIG. 2 diagrammatically shows views in two longitudinal sections of distal ends of ablation catheters, and FIG. 3 diagrammatically illustrates an embodiment of an arrangement with an ablation catheter with cooled wires.

DETAILED DESCRIPTION OF THE INVENTION

Figure 2B:
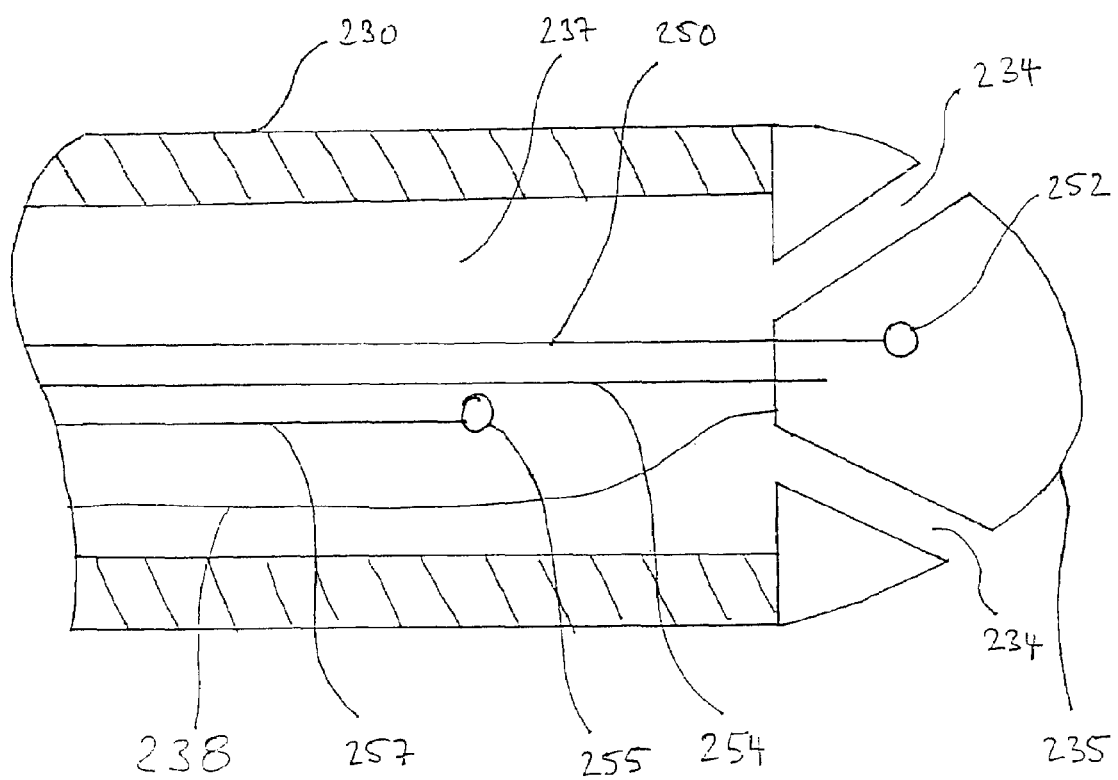

The invention will now be described in greater detail with reference to Figures.

FIG. 1a diagrammatically shows a view in cross-section of a catheter 101. The catheter 101 includes a catheter shaft having a shaft wall 102 and a first lumen 104 which is enclosed by the shaft wall 102. Disposed in the lumen 104 are wires 106 which can be in the form of electrical feed lines. Disposed in the lumen 104 there is also a second lumen 105 which is enclosed by a second shaft wall 107. A wire 103 to be cooled is disposed in the second lumen 105. The shaft walls 102 and 107 are of fluid-tight nature.

When using a catheter with such a catheter shaft cross-section, a fluid, for example a cooling fluid, can flow, for example through, the second lumen 105.

The through-flow of fluid can be in the form of a unidirectional flow. For that purpose, in the region of the proximal end, the catheter has an intake for the fluid, while in the region of the distal end it has an outlet for the fluid.

The through-flow of fluid can also be in the form of a counter-flow. For that purpose, in the region of the distal end the catheter has a fluid passage (not shown in this Figure) through which the lumens 105 and 104 are in fluid communication in the region of the distal end. The fluid can now flow, for example, in the second lumen 105 in the direction of the distal end and can flow back through the first lumen 104 by way of the fluid passage to the proximal end of the catheter. It is also possible to conceive of a reversed direction of flow so that the fluid flows in the first lumen 104 to the distal end and back in the second lumen 105 to the proximal end.

FIG. 1b shows a view in cross-section through a catheter shaft 121 with a shaft wall 122 which encloses a first lumen 127 and a second lumen 126. The first lumen 127 and the second lumen 126 are separated from each other by a separating wall 125. An electrically conductive wire 123 and electrical feed lines 124 are disposed in the second lumen 126. The shaft wall 122 and the separating wall 125 are of a fluid-tight nature.

By way of example, a fluid can flow in the second lumen to the distal end of the catheter, it can be passed in the region of the distal end through a fluid passage (not shown) into the first lumen 127 and there it can flow back to the proximal end of the catheter.

FIG. 1c shows a view in cross-section through a catheter shaft 131 with a fluid-tight shaft wall 132 which encloses a lumen 135. The lumen 135 can have, for example, a heat-insulating foam. The lumen 135 contains a first lumen 134 enclosed by a first shaft wall 138. The lumen 135 further contains a second lumen 133 which is enclosed by a second shaft wall 137 and has a wire 136. For example, a fluid can flow through the second lumen 133 and the first lumen 134. In that case, for example, the fluid flows in the first and second lumens in respectively opposite directions. For that purpose, the first shaft wall 138 and the second shaft wall 137 are of fluid-tight nature.

FIG. 1d shows a view in cross-section through a catheter shaft 141 having a shaft wall 142 which encloses a first lumen 146. Arranged in the first lumen 146 is a second lumen 143 which is enclosed by a second shaft wall 147. A wire 144 is mounted by means of a heat-conductive adhesive 145 on the surface of the second shaft wall, which faces towards the first lumen. The second lumen 143 can guide a fluid. In this embodiment, the fluid in the second lumen can receive heat which is given off by the wire 144 and which is passed by way of the heat-conductive adhesive 145 and the second shaft wall 147 to the fluid. For that reason, the second shaft wall 147 is of a fluid-tight and heat-conducting nature. The heat-transmission resistance formed in this arrangement in respect of the lumen 146 from the wire 144 to the shaft wall 142 is higher than the heat-transmission resistance from the wire 144 to the lumen 143, formed by the heat-conductive adhesive 145 and the heat-conductive second shaft wall 147.

FIG. 1e shows a view in cross-section through a catheter shaft 151 with a fluid-tight shaft wall 152 which encloses a lumen 153. The lumen 153 can have for example a heat-insulating foam. The lumen 153 contains a first lumen 158 which is enclosed by a first shaft wall 157. The lumen 153 further contains a second lumen 154 which is enclosed by a second shaft wall 155 and has a wire 156. The lumen 153 further contains a third lumen 159 which is enclosed by a shaft wall 160. The three lumens 154, 158 and 159 can have a fluid flowing therethrough. In that case, the fluid flows, for example, in the first lumen 158 and in the second lumen 154 in the same direction, for example, to the distal end of the catheter, and in the third lumen 159 in the opposite direction thereto, for example to the proximal end of the catheter. For that purpose, the shaft walls 155, 157 and 160 are of a fluid-tight nature.

FIG. 2a is a diagrammatic view in longitudinal section of the distal end of an ablation catheter 201 with a shaft wall 203 which extends from the distal end of the catheter to the proximal end thereof and which encloses a first lumen 209 and a second lumen 207. The lumens 209 and 207 are separated from each other by a separating wall 211 arranged along the catheter longitudinal axis, wherein the separating wall 211 at the distal end of the catheter has a fluid passage in the form of an aperture 208. Mounted to the outer distal end of the catheter is an electrode 205 which, by way of a heat-conductive, electrically insulating layer 206, is in thermal contact with the lumen 207 and with the lumen 209. The shaft wall 203, the separating wall 211 and the insulating layer 206 are of fluid-tight nature. The electrode 205 has an electrode temperature sensor 222 which is connected to an electrical connecting line 220 which extends along the catheter longitudinal axis to the proximal end of the catheter and which is arranged in the second lumen 207. The catheter also includes a fluid temperature sensor 226 which is arranged in the region of the distal end of the catheter 201 in the first lumen 209 and which is connected to an electrical connecting line 227 extending along the catheter longitudinal axis to the proximal end of the catheter in the first lumen. In the region of the distal end, the catheter also includes a wire temperature sensor 228 which is connected to a connecting line 229 extending in the second lumen to the proximal end of the catheter and which is arranged in the second lumen 207.

When a fluid flows in the second lumen 207 to the distal end of the catheter and flows back by way of the aperture 208 and the first lumen to the proximal end of the catheter, the increase in temperature of the fluid caused by the wires is detected by the temperature sensor 228, the temperature of the electrode 205 is detected by the electrode temperature sensor 222 and the temperature of the fluid after receiving the heat of the electrode head, which is given off by way of the insulating layer 206, is detected by the temperature sensor 226. The catheter also has a feed line wire 224 which is passed in the second lumen 204 from the distal end of the catheter to the proximal end thereof along the catheter longitudinal axis and is fixed at the distal end of the catheter. The feed line wire 224 is of an electrically conducting nature and is electrically connected to the electrode 205. In this embodiment, high-frequency energy can be fed to the electrode 205 by way of the electrically conducting feed line wire 224.

FIG. 2b diagrammatically shows a view in longitudinal section of the distal end of an ablation catheter 230 with a shaft wall 203 which extends from the distal end of the catheter to the proximal end and which encloses a lumen 237. Mounted to the outer distal end of the catheter is an electrode 235, which is electrically connected to the proximal end of the ablation catheter 230 by way of a feed line wire 238. The feed line wire 238 extends in the lumen 237. The shaft wall 203 is of a fluid-tight nature. The electrode 205 has an electrode temperature sensor 252 which is connected to an electrical connecting line 250 extending along the catheter longitudinal axis to the proximal end of the catheter and which is arranged in the lumen 237. The catheter also includes a wire temperature sensor 255, which is arranged in the lumen 237 in the region of the distal end of the catheter 230 and which is connected to an electrical connecting line 257 extending to the proximal end of the catheter in the first lumen along the catheter longitudinal axis. The electrode 235 has openings 234 which are in fluid communication with the lumen 237 so that fluid can flow outwardly through the openings.

FIG. 3 shows an arrangement 301 with a supply device 330 and an ablation catheter which is connected to the supply device 330 by way of a socket 332.

The ablation catheter includes a catheter shaft 306 which opens into a handle 336, the handle 336 being connected to a flexible hose 333. Mounted to the flexible hose 333 at the end is a plug 331 which can be connected to the socket 332.

The distal end of the catheter shaft 306 is shown in an enlargement window 302 in FIG. 3. The catheter shaft 306 has a shaft wall 303 which encloses a first lumen 309 and a second lumen 307. The first lumen 309 and the second lumen 307 are separated from each other by a separating wall 311. The arrangement of the shaft wall 303, the first lumen 309, the second lumen 307 and the separating wall 311 is similar to the structure shown in cross-section in FIG. 1b. The first lumen 309, the second lumen 307 and the separating wall 311 are provided from the distal end of the catheter shaft 306 to the proximal end of the catheter shaft 306. The catheter shaft has a control wire 328 which is fixed at the distal end of the catheter shaft and which is guided along the catheter longitudinal axis in the first lumen 309 into the handle 336, the control wire 328 being connected to the slider 337 in the handle 336. Actuation of the slider 337 causes curvature of the distal end of the catheter with a directional component in orthogonal relationship with the catheter longitudinal axis. An ablation electrode 305 is mounted at the outer distal end of the catheter shaft. The ablation electrode is in the form of a bipolar electrode, and for that purpose, includes a counterpart electrode 304 which is in the form of a ring electrode at the distal end of the catheter shaft. The catheter shaft has an electrode temperature sensor 322, which is mounted to the high-frequency electrode 305 and connected to a temperature sensor line 320, which opens through the second lumen 307 into the handle 336, along the catheter longitudinal axis. A wire temperature sensor 325 is arranged in the region of the distal end in the second lumen 307 and is connected to the temperature sensor line 320, which is in the form of a two-channel temperature sensor line. A fluid temperature sensor is arranged in the region of the distal end of the catheter in the first lumen and is connected to an electrical fluid temperature sensor line 327, which is guided along the catheter longitudinal axis in the first lumen and which opens into the handle 336. The high-frequency electrode 305 and the counterpart electrode 304 are connected to a two-channel high-frequency line 324, which is guided in the second lumen along the longitudinal axis of the electrode line and opens into the handle 336. The first lumen 309, the fluid temperature sensor line 327 and the temperature sensor line 320 are brought together in the handle 336 to constitute a line bundle 335, which communicates with the plug 331. A first fluid line 353, a second fluid line 352, an electrical high-frequency line 368 and a three-channel temperature sensor line 366 open into the socket 332 of the supply device 330. When the plug 331 is coupled to the socket 332 the first fluid line 353 is in fluid communication with the first lumen 309, the second fluid line 352 is in fluid communication with the second lumen 307, the electrical high-frequency line 368 is electrically connected to the high-frequency line 324 and the three-channel temperature sensor line 366 is electrically connected to the fluid temperature sensor line 327 and the temperature sensor line 320.

The supply device 330 includes a fluid feed unit 344 having a. circulation pump 374 connected to fluid lines 355 and 354. The supply device 330 also has a controllable cooling unit 342 with a control input having a thermostat for maintaining a predetermined fluid temperature. The cooling unit 342 is connected to the fluid lines 354, 355, 352 and 353, wherein the fluid line 355 is in fluid communication by way of the cooling unit 342 with the second fluid line 352 and the fluid line 354 is in fluid communication by way of the cooling unit 342 with the first fluid line 353. The cooling unit 342 is preferably in the form of a Peltier cooling unit and for that purpose includes at least one Peltier element. The arrangement 301 also includes a fluid feed container 358 which is connected by way of a fluid feed line 356 to the fluid feed unit 344 and there is connected by way of an inlet valve 378 contained in the fluid feed unit to the pump intake 377 to which the fluid line 354 is also connected. The arrangement 301 also includes a fluid discharge container 359 into which opens a fluid discharge line 357, which, by way of an excess pressure valve 376 contained in the fluid feed unit 344, is in fluid communication with the circulation pump outlet 375 upon opening of the excess pressure valve 376. The circulation pump outlet 375 is connected to the fluid line 355. The valves 376 and 378 as well as the pump 374 are adapted to be controllable. For that purpose, the fluid feed unit 344 has a control input and is connected by way of a control line 360 to the control output of a temperature monitoring and control unit 346. The fluid feed unit 344 is adapted, on the basis of the control information of a control signal received by way of the control line 360, selectively to set the pump volume of the circulation pump 374 or to open or close the valves 378 and 376. The temperature monitoring and control unit 346 is connected at the output side by way of an electrical connecting line 362 for controlling the cooling unit 342 to the control input thereof. The cooling unit 342 is adapted to cool a fluid flowing through the cooling unit 342, on the basis of a control signal received by way of the control line. The cooling unit 342 can also be adapted to set a fluid temperature or cooling efficiency corresponding to the control signal. For that purpose, the cooling unit 342 can include a temperature regulator. The temperature monitoring and control unit is operatively connected by way of a three-channel temperature sensor line 366 to the temperature sensors 325, 326 and 322 contained in the catheter shaft.

The fluid temperature sensor 326 can also be arranged in the handle 336 alternatively to the arrangement in the first lumen 309 of the catheter shaft 306 and there is also arranged in the first lumen 309 or is connected in heat-conductive relationship to the first lumen 309.

The supply device 330 also includes a high-frequency generator 340 which is connected by way of an electrical high-frequency line 368 and by way of an electrical high-frequency line 324 to the high-frequency electrode 305 and the counterpart electrode 304. The electrical high-frequency lines 368 and 324 are of a two-channel configuration for that purpose. The high-frequency generator 340 is connected by way of a high-frequency control line 364 to the temperature monitoring and control unit 346. The temperature monitoring and control unit 346 is connected to an input unit 380 by way of a bidirectional data bus 381, the input unit being connected to a display 382 by way of a connecting line 383.

The mode of operation of the arrangement will now be described in greater detail:

Operating parameters for operation of the ablation catheter can be input into the temperature monitoring and control unit 346 by way of the input unit 380 which includes, for example, a keypad. The parameters are, for example, switching a high-frequency power on or off or preselecting a predetermined high-frequency power which is to be delivered by way of the high-frequency electrode 305 or preselecting a desired ablation electrode temperature. The temperature monitoring and control unit 346, which, for example, comprises a microprocessor, is adapted, in accordance with the setting by the input unit 380, to send a signal corresponding to the input value to the high-frequency generator 340 by way of the high-frequency control line 364 for producing a high-frequency power corresponding to the input value. The high-frequency generator 340 is adapted, on the basis of the control signal received by way of the high-frequency control line 364, to deliver a high-frequency power corresponding to the input value by way of the electrical high-frequency line 368 and the high-frequency electrode 305 operatively connected thereto. The temperature sensors 325, 326 and 322 are adapted to produce a temperature signal representative of the detected temperature. The temperature signals respectively produced by the temperature sensors are available to the temperature monitoring and control unit 346 by way of the temperature sensor lines 327 and 320 respectively connected to the temperature sensors and by way of the three-channel temperature sensor line 366.

The temperature monitoring and control unit 346 is adapted to evaluate the temperature signals received by way of the three-channel temperature sensor line 366 and to control the pump volume of the circulation pump 374 by way of the connecting line 360, the cooling output of the cooling unit 342 by way of the connecting line 362 and the high-frequency power by way of the high-frequency control line 364, in accordance with a regulating algorithm which is predetermined in the temperature monitoring and control unit 346, and to produce control signals corresponding thereto. The temperature monitoring and control unit 346 can send signals corresponding to items of status information by way of the bidirectional data bus 381, the input unit 380 and the connecting line 383 to the display 382 which can display those items of status information. The items of status information can be for example the temperature of the high-frequency electrode 305, the temperature, detected by the fluid temperature sensor 326, of the fluid 370 which is in the first lumen 309, and the temperature, detected by the wire temperature sensor 325, of the fluid 370, which is in the second lumen 307. The temperature monitoring and control unit 346 is also adapted to evaluate a signal received by way of the connecting line 366 from a fluid sensor, which is mounted in the fluid feed unit and to monitor the fluid filling level and/or the fluid pressure in the fluid circuit formed by the fluid lines and the lumens and to suitably control the inlet valve 378 for the intake of a fluid 370 into the fluid circuit by way of the fluid feed line 365. In the event of an excess pressure in the fluid circuit, produced by the rise in temperature of the catheter shaft, the excess pressure valve 376 is adapted to open at a predetermined excess pressure and thus to discharge excess fluid 372 into the fluid discharge container 359 by way of the fluid discharge line 357.

The features set forth in the specific description can also be embodied considered in themselves independently of the other features set forth in this connection on a catheter or an arrangement with a catheter.

The invention claimed is:

1. A catheter for intravascular application, with a proximal and a distal end and a catheter longitudinal axis, the catheter comprising:
   a shaft extending along the catheter longitudinal axis from the proximal end to the distal end and having a fluid-tight shaft wall
   and at least one lumen which is adapted to guide a fluid, which extends from the proximal end at least into the proximity of the distal end of the catheter and which is enclosed by the shaft,
   at least one electrically conductive wire which extends from the proximal end at least into the proximity of the distal end of the catheter along the catheter longitudinal axis,
   wherein at least one portion of the length of the catheter which is adapted for introduction into a body and is further adapted to provide
   a lower level of heat-transmission resistance obtains between a fluid in the lumen and the electrically conductive wire than between the wire and the shaft wall so that heat produced in the wire can be effectively dissipated to the fluid flowing in the lumen,
   wherein the catheter includes at least one temperature sensor which is arranged to detect a temperature which, in the case of heating of the wire, depends at least predominantly on the heating of the wire.

2. A catheter as set forth in claim 1, characterized in that the catheter has a first and a second lumen which are adapted to guide a fluid, which extend from the proximal end of the catheter into the proximity of the distal end of the catheter and which are enclosed by the shaft, and in the region of the distal end the catheter has a fluid passage between the first lumen and the second lumen so that fluid can flow in the first lumen in the direction of the distal end and from there into the fluid passage and in the second lumen back to the proximal end.

3. A catheter as set forth in claim 1, characterized in that in the proximity of the distal end, the catheter has at least one opening which is in fluid communication with at least one of the lumen and which is so designed that fluid can flow outwardly from the catheter.

4. A catheter as set forth in claim 3, characterized in that the catheter has at least one temperature sensor which is arranged along the longitudinal axis of the catheter in the region of the portion of the catheter shaft which is provided for intracorporeal invasion, spaced from ablation electrodes.

5. A catheter as set forth in claim 3, characterized in that the catheter shaft has three lumens which are respectively adapted to guide a fluid and of which a lumen in the form of a wire-guiding lumen in which at least one wire to be cooled is arranged.

6. A catherter as set forth in claim 1, characterized in that the catheter additionally has at least one second temperature sensor adapted for detecting the temperature of the fluid or of the shaft wall.

7. A catheter as set forth in claim 1, characterized in that the wire is an electrical feed line.

8. A catheter as set forth in claim 1, characterized in that the wire is a control wire which is arranged displaceably in an inner lumen in the direction of the catheter longitudinal axis.

9. A catheter as set forth in claim 1, characterized in that the catheter comprises, along the catheter longitudinal axis, a plurality of temperature sensors which are so arranged as to detect the temperature of the wire, the shaft wall, a lumen, or a combination thereof 10. A catheter as set forth in claim 1, characterized in that the catheter is an ablation catheter.

11. A catheter as set forth in claim 10, comprising an ablation electrode and three lumens, characterized in that at least one wire to be cooled is arranged in a first lumen and the distal end is adapted to feed exclusively a fluid flowing in a second lumen to the ablation electrode for cooling purposes, and to return the fluid in a third lumen to the proximal end.

12. A catheter as set forth in claim 1, characterized in that the catheter is a guide wire.

13. A catheter as set forth in claim 1, characterized in that the catheter is a mapping catheter.

14. An arrangement for intravascular invasion including a catheter as set forth in claim 1, and
a fluid feed unit which is in fluid communication with at least one lumen of the catheter and adapted to produce a fluid flow into the lumen.

15. An arrangement as set forth in claim 14, characterized in that the fluid feed unit includes a controllable pump unit which is in fluid communication at least with one lumen of the catheter and which is adapted to pump a fluid into the lumen in dependence on a fluid control signal.

16. An arrangement as set forth in claim 15, characterized in that the arrangement has a temperature monitoring unit which is operatively connected to at least one temperature sensor, the pump unit or a cooling unit or both, wherein the temperature sensor is adapted to produce a temperature signal representative of a temperature and the temperature monitoring unit is adapted to evaluate a temperature signal produced by the temperature sensor and to control the pump unit or the cooling unit or both in accordance with a regulating algorithm predetermined in the temperature monitoring unit and to produce control signals corresponding thereto.

17. An arrangement as set forth in claim 14, characterized in that the arrangement includes a cooling unit which is in fluid communication with at least one lumen of the catheter and the cooling unit is adapted to take heat from a fluid in dependence on a cooling control signal.

18. An arrangement as set forth in claim 17, characterized in that the arrangement has a temperature monitoring unit which is operatively connected to at least one temperature sensor, a pump unit or the cooling unit or both, wherein the temperature sensor is adapted to produce a temperature signal representative of a temperature and the temperature monitoring unit is adapted to evaluate a temperature signal produced by the temperature sensor and to control the pump unit or the cooling unit or both in accordance with a regulating algorithm predetermined in the temperature monitoring unit and to produce control signals corresponding thereto.

* * * * *